United States Patent
Spence et al.

(10) Patent No.: US 6,797,002 B2
(45) Date of Patent: Sep. 28, 2004

(54) HEART VALVE REPAIR APPARATUS AND METHODS

(75) Inventors: Paul A. Spence, 5818 Orion Rd., Louisville, KY (US) 40222; Mark Ortiz, Milford, OH (US)

(73) Assignee: Paul A. Spence, Louisville, KY (US)

(*) Notice: Subject to any disclaimer, the term of this patent is extended or adjusted under 35 U.S.C. 154(b) by 0 days.

(21) Appl. No.: 10/268,028

(22) Filed: Oct. 9, 2002

(65) Prior Publication Data

US 2003/0083742 A1 May 1, 2003

Related U.S. Application Data

(63) Continuation of application No. 09/496,450, filed on Feb. 2, 2000, now abandoned.

(51) Int. Cl.[7] .................................................. A61F 2/06
(52) U.S. Cl. ........................................................ 623/2.38
(58) Field of Search .............................. 623/236, 2.37, 623/2.38, 2.1, 2.17, 2.14, 2.18

(56) References Cited

U.S. PATENT DOCUMENTS

| | | | |
|---|---|---|---|
| 3,130,418 A | 4/1964 | Head et al. .................... 3/1 |
| 4,021,863 A | 5/1977 | Woien ........................... 3/1.5 |
| 4,106,129 A | 8/1978 | Carentier et al. ............. 3/1.5 |
| 4,164,046 A | 8/1979 | Cooley ......................... 3/1.5 |
| 4,261,342 A | 4/1981 | Aranguren Duo ........... 128/1 R |
| 4,275,469 A | 6/1981 | Gabbay ........................ 3/1.5 |
| 4,339,831 A | 7/1982 | Johnson ........................ 3/1.5 |
| 4,340,977 A | 7/1982 | Brownlee et al. ............ 3/1.5 |
| 4,489,446 A | 12/1984 | Reed ............................ 3/1.5 |
| 4,602,911 A | 7/1986 | Ahmadi et al. .............. 623/2 |
| 4,655,773 A | 4/1987 | Crassi ........................... 623/2 |
| 4,917,698 A | 4/1990 | Carpentier et al. .......... 623/2 |
| 4,960,424 A | 10/1990 | Grooters ....................... 623/2 |
| 5,061,277 A | 10/1991 | Carpentier et al. .......... 623/2 |
| 5,104,407 A | 4/1992 | Lam et al. .................... 623/2 |
| 5,163,955 A | 11/1992 | Love et al. ................. 623/2.15 |
| 5,171,252 A | 12/1992 | Friedland ................... 227/902 |
| 5,201,880 A | 4/1993 | Wright et al. ................ 623/2 |
| 5,306,296 A | 4/1994 | Wright et al. ................ 623/2 |
| 5,332,402 A | 7/1994 | Teitelbaum ................... 623/2 |
| 5,360,444 A | 11/1994 | Kusuhara ...................... 623/2 |
| 5,397,351 A | 3/1995 | Pavcnik et al. ............. 623/11 |
| 5,415,667 A | 5/1995 | Frater ............................ 623/2 |
| 5,449,384 A | 9/1995 | Johnson ........................ 623/2 |
| 5,450,860 A | 9/1995 | O'Connor .................. 128/898 |
| 5,545,214 A | 8/1996 | Stevens ......................... 623/2 |

(List continued on next page.)

OTHER PUBLICATIONS

F. Maisano et al., *The edge–to–edge technique: a simplified method to correct mitral insufficiency*, European Journal of Cardio–thoracic Surgery 13, pp. 240–246, 1998.

Carlos M.G. Duran, M.D., Ph.D., *Perspectives in Reparative Surgery for Acquired Valvular Disease*, Advances in Cardiac Surgery®, vol. 4, 1993.

*Primary Examiner*—Corrine McDermott
*Assistant Examiner*—William Matthews
(74) *Attorney, Agent, or Firm*—Wood, Herron & Evans, L.L.P.

(57) ABSTRACT

Valve repair apparatus and methods for ensuring proper coaptation and operation of the leaflets of a heart valve. Main aspects of the disclosure relate to devices including a support member configured for attachment to the heart valve annulus, a post extending from the support member away from the plane of the annulus and a connector coupled with the post and configured for attachment to at least one of the leaflets. The various embodiments may include a replacement heart valve connected with the support member for facilitating full replacement as opposed to near repair of an existing native heart valve. Various other devices include support structure and one or more posts connected to opposite sides of the support structure and extending from one side of the valve annulus to another to modify the shape of the annulus.

15 Claims, 12 Drawing Sheets

U.S. PATENT DOCUMENTS

| | | | |
|---|---|---|---|
| 5,549,665 A | 8/1996 | Vesely et al. | 623/2.14 |
| 5,554,184 A | 9/1996 | Machiraju | 623/2 |
| 5,554,185 A | 9/1996 | Block et al. | 623/2 |
| 5,662,704 A | 9/1997 | Gross | 623/2 |
| 5,674,279 A | 10/1997 | Wright et al. | 623/2 |
| 5,709,695 A | 1/1998 | Northrup, III | 606/148 |
| 5,716,397 A | 2/1998 | Myers | 623/2 |
| 5,733,331 A | 3/1998 | Peredo | 623/2 |
| 5,824,065 A | 10/1998 | Gross | 623/2 |
| 5,824,066 A | 10/1998 | Gross | 623/2 |
| 5,824,067 A | 10/1998 | Gross | 623/2 |
| 5,855,601 A | 1/1999 | Bessler et al. | 623/2 |
| 5,888,240 A | 3/1999 | Carpentier et al. | 623/2 |
| 5,908,450 A | 6/1999 | Gross et al. | 623/2 |
| 5,931,868 A | 8/1999 | Gross | 623/2 |
| 6,332,893 B1 | 12/2001 | Mortier et al. | 623/2.1 |

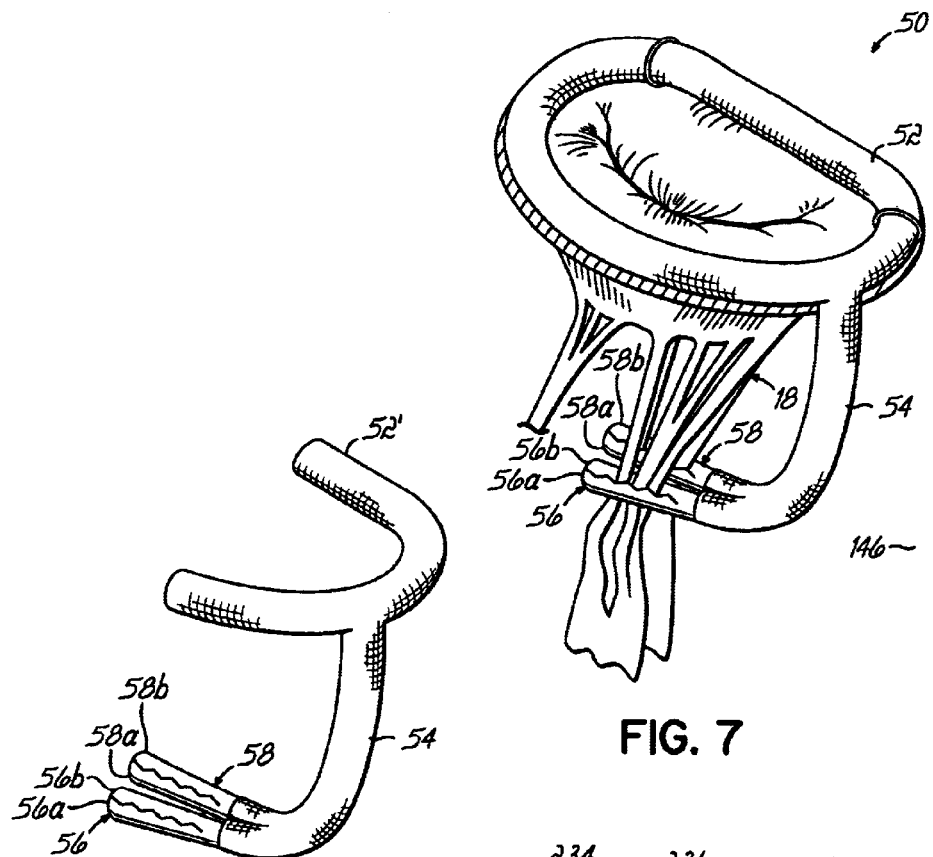
FIG. 7
FIG. 7A
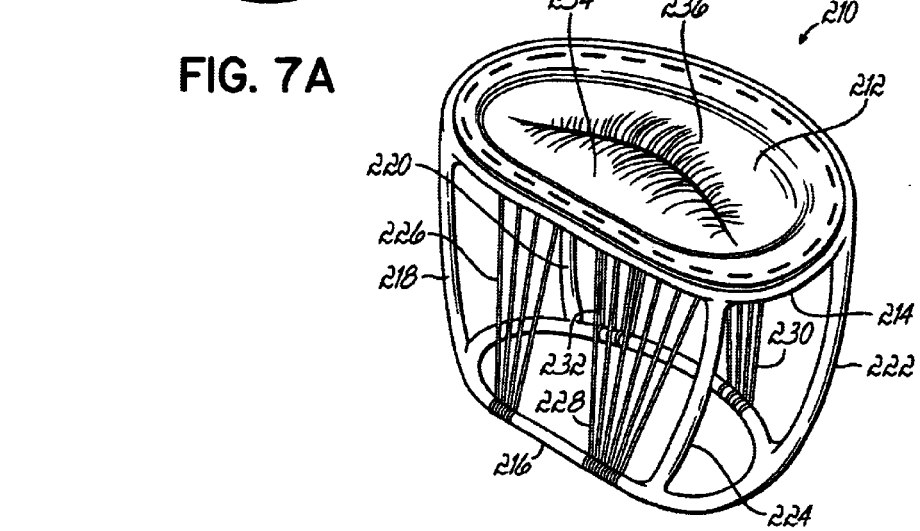
FIG. 15

HEART VALVE REPAIR APPARATUS AND METHODS

This application is a continuation of application Ser. No. 09/496,450 filed Feb. 2, 2000 (now abandoned), the disclosure of which is fully incorporated herein by reference.

FIELD OF THE INVENTION

The present invention generally relates to heart valve repair and replacement techniques and apparatus. More specifically, the invention relates to the repair of heart valves having various malformations and dysfunctions.

BACKGROUND OF THE INVENTION

The mitral valve depends on adequate apposition or alignment between the anterior and posterior leaflets along a relatively long surface area under high pressure conditions. Typically, the contact surface is about 12 mm in a direction perpendicular to the anterior-posterior direction and this provides little margin of safety. The leaflet margins are attached to numerous fine chords suspended from attachment points along the inner surface of the left ventricle. Although these attachments are often referred to as papillary muscles, there is often a very diffuse arc-shaped attachment for each of the groups of chords to the endocardial surface. Unfortunately, this anchor point (i.e., the inner wall of the left ventricle) must move with each heartbeat and so the distance between the attachment of the leaflet edges is constantly changing. The chordal lengths may also change—typically increasing with age and degeneration and the chords frequently do not lengthen in a symmetrical fashion. This leads to variations in their lengths at all-important points of coaptation. Chords may also rupture. In addition, the mitral annulus changes diameter with each heartbeat such that it surface area changes by about 40% with each systole. As the heart enlarges, the annulus of the mitral valve can enlarge as well. In short, there are many variables affecting proper functioning of the mitral valve. The anatomy, such as the leaflet length, the chordal length and the annular length/diameter can change. The attachment points can change as the ventricle changes shape. More importantly, all of these aspects can change simultaneously. For example, a patient may have ischemic mitral regurgitation which pulls the posterolateral valve attachments away from their natural coaptation points and leads to an opening in this area of the mitral valve. This can be further affected if the chordal lengths are changed by even minor degrees of degenerative disease.

Mitral valve pathology has changed remarkably since the origin of open heart surgery one generation ago. Initially, the most common pathology or condition was rheumatic mitral valve disease. This produced thickened, impliable leaflets with grossly deformed chords, or chordae tendinae, often combined with fusion of the two leaflets. This valve was not suitable for any type of plastic procedure and, accordingly, numerous valve prostheses were developed to replace the entire valve, i.e., the annulus, leaflets and chords. Now, except in centers with high rates of immigration from third world countries, rheumatic mitral valve disease is a relatively uncommon indication for surgery. Various forms of degeneration ranging from gross billowing of leaflets to relatively minor chordal lengthening as well as ischemic mitral valve pathology are most commonly encountered. Recently, it has become apparent that combinations of these two problems are relatively common. In both of these situations, the mitral valve leaflets are soft, pliable and can be retained over the long-term in various repair procedures. Unfortunately, despite the fact that the leaflet tissue is suitable for retention, mitral repair is performed for less than half of the cases where mitral regurgitation is the problem. In surgical centers where mitral repair is not practiced, valves are often discarded and replaced.

One main problem is that mitral valve repair technology has not kept pace with the change in mitral valve pathology. Mitral valve repair is more an art than a science and requires a constant interaction between visual inspection and post operative results, as evidenced by transesophageal echocardiography (TEE). Few surgeons or surgical centers are equipped for or capable of performing this type of work on a routine basis. Many surgeons only perform mitral annuloplasty with rings that reduce the diameter of the annulus. These rings may appear to be a solution for a variety of problems but are not ideal for many ischemic and degenerative disease conditions.

Despite many attempts, the homograft mitral valve replacement is not an operation which can be performed reliably. It could have potential advantages in third world countries or in cases of infection. Failures occur because of the unreliability of attachment of the chords to the left ventricle. It is not difficult to anchor the valve in the annulus. However, it is virtually impossible to ensure that the chords are correctly spaced inside the ventricle to produce a competent valve. Again, the inner surface of the ventricle is a moving surface and it is almost impossible to guarantee that a chord extending from a leaflet edge will be fixed in such a way that the anterior and posterior leaflets are reliably aligned during valve operation.

Various other repair procedures are performed, but these are limited to the removal of leaflet tissue which is poorly supported and to chordal shortening and replacement. Many valves simply remain unrepaired due to the shortage of acceptable techniques and apparatus. The sophisticated procedures are acquired art forms that many surgeons either cannot master or do not have the time and opportunity to master.

Thirty years of valve surgery have indicated that the native leaflet tissue is the most reliable valve material. Despite numerous attempts to produce durable leaflet replacements, none have been found. The cost of demonstrating the value of a new material is extremely high. However, chordal replacement with polytetrofluorethylene is durable and highly satisfactory. Therefore, this at least provides a proven, reliable material to suspend leaflet tissue.

It is also clear that annuloplasty rings are durable, well-tolerated and do not require long-term anticoagulation. They fix the annular dimensions and reliably reduce one of the most important variables (i.e., the mitral annulus diameter) in mitral valve competence.

Regulatory issues in this field are the single most expensive factor. Next generation valve prosthesis designs are therefore most desirably based on the numerous available annuloplasty devices.

To properly and consistently repair the mitral valve, these variables must be fixed—the annular diameter, the leaflet length, the chordal length and the attachment point of the chords. Fortunately, the leaflet length is relatively constant. The annulus diameter can be fixed by the annuloplasty ring. The chords can be replaced by polytetrofluorethylene suture to fix their length. The missing variable is the attachment of the chords to the left ventricle. To date, this remains a troublesome variable to the valve repair.

Ischemic mitral regurgitation occurs when there is ventricular dysfunction which causes the posterolateral attachments of the mitral valve to be drawn away from the annulus in systole. This pulls the two leaflet edges apart at their point of coaptation and produces an asymmetrical regurgitant jet or, in other words, blood flow in the wrong direction through the valve. In its pure form, the leaflets, the chords and the attachment points are all anatomically normal. Sometimes there is a relative discrepancy between the distance the anterior leaflet is drawn inward relative to the posterior leaflet so they are not just separated from edge-to-edge but also there is a step deformity of the junction point. The patient may also have some underlying mild degree of degenerative deformity which may initially cause a mild, but well-tolerated degree of mitral regurgitation. However, the regurgitation often becomes severe after left ventricular ischemia occurs.

Some repair techniques apply tight annuloplasty rings which serve to buckle the leaflets and draw them together. This often leaves a degree of mitral regurgitation and mitral stenosis results. Annuloplasty can be accompanied by a modification of the Alfieri edge-to-edge repair, more recently referred to as the bowtie repair. With this technique, the surgeon merely sews the anterior leaflet to the posterior leaflet at the point of maximal distraction. This produces a two orifice valve with more stenosis.

Devices and methods are necessary that preserve the leaflet tissue but provides for virtually guaranteed coaptation of the leaflets by fixing some of the variables responsible for regurgitation. Other devices and methods are necessary that do not simply reduce the diameter of a heart valve annulus, but allow more specialized treatment tailored to patient needs.

SUMMARY OF THE INVENTION

Degenerative disease generally involves a relatively normal leaflet which is poorly supported by lengthened or ruptured chords. By attaching the poorly supported leaflet to replacement or native chords connected with a post in the left ventricle, a guaranteed point of coaptation can be produced. In this regard, one general form of the invention provides a device for supporting a heart valve in a patient with the heart valve including an annulus generally lying in a plane and a plurality of leaflets connected therewith and adapted to open and close to selectively allow and prevent blood flow. The device comprises a support member configured for attachment to the heart valve and the above-mentioned post extending from the support member and configured to extend away from the plane of the annulus. A connector is coupled with the post and configured for attachment to at least one of the leaflets. The post can support the posterior leaflet (extending from the posterior part of the support member), the anterior leaflet (extending from the anterior part of the support member) or both leaflets. For example, this would require a relatively simple modification of the currently available annuloplasty rings or other support members, for example, which may be ring segments. The connector may be one or more flexible tensile members, such as replacement chords passing from the leaflet(s), through or along the post and up to the support member. These flexible tensile members may be precisely length adjusted to bring the unsupported leaflet edge to the precise depth. This could replace the current posterior leaflet resection. It would also be a solution for the anterior leaflet repair which has produced only marginal results in most hands. The invention is also applicable to replacement heart valves formed of biologic or artificial materials. Various aspects of the invention are applicable to the repair of native valves, while other aspects apply to replacement valves of artificial biocompatible material, animal valve tissue or human valve tissue.

A device constructed in accordance with the invention would preferably fix the annular diameter, the chordal length and the point of chordal fixation in the ventricle. In this way, the invention provides a more reliable and permanent solution to the problems associated with the valve repair. Furthermore, it would be easy to perform by most surgeons. A small incision could be made in the annular attachment of the poorly supported anterior leaflet and the post passed through this incision. The support member would then be attached to the native annulus. Flexible tensile members, such as artificial or natural chords would then be attached from the post to the unsupported edge of the leaflet and adjusted by pulling them to length and fixing them. In the case of replacement chords, they are preferably fixed at the level of the support member. Devices could include posterior posts, anterior posts or both. A variety of possibilities exist for modified structures, including multi-forked posts or surgeon-created posts. It would also be preferable to provide chordal patterns to attach the posts to the leaflets and to develop a quick connect system for attachment of the chords to the leaflet edges. Adjustability of the system will be important in many cases for fine tuning.

Another form of the invention comprises a support member, which may be an annuloplasty ring or other support structure, and at least one post. A first chord gripping member is coupled with the post and configured to grip at least one of the chords and thereby fix the length of the chord between the first gripping member and the leaflets to support and align the leaflets for coaptation during operation of the valve. In the case of mitral valve repair, the post extends into the left ventricle taking origin from the posterolateral commisure. In a preferred embodiment, one gripping member traps the chords to the anterior leaflet in such a way that their distance from the leaflet edge is precisely fixed. A second post and gripping member can do the same for the posterior leaflet. The surgeon would then confirm that the gripping members had captured the chords precisely so that the leaflets meet exactly in systole. If there would be any doubt about this coaptation or should there be a fear of late failure due to chordal rupture, the native chords could be augmented or replaced by an array of replacement chords suspended from the posts and attaching to the leaflet edge. One may also postulate improved left ventricular function from the device since the bulging of the posterior wall of the heart will be prevented by the tethering of the chords which are trapped in the device.

The various devices of this invention are formed of biocompatible materials including, but not limited to, exposed biocompatible metals, fabric covered metal or polymer, exposed polymer, or any other biocompatible artificial or biologic material. The various devices of this invention may also be incorporated into a full replacement heart valve structure again formed from any biocompatible material for cases necessitating full replacement of the valve. In these cases, the replacement valve is fully supported in a position ensuring accurate coaptation of the valve leaflets and less stressful interaction of the valve leaflets with each other as well as with the valve commisures.

Another aspect of the invention provides a device for supporting a heart valve in a patient comprising a support structure configured for attachment to the heart valve annulus and a post connected to opposite sides of the support structure and configured to extend from one side of the annulus to another side thereof. This modifies the shape of the annulus, for example, to correct for ischemic condition.

The post may be contained substantially in the same plane as the support structure and valve annulus or may extend substantially out of the plane containing the support structure and valve annulus. If extending substantially in the same plane, the post prevents outward bellowing of the valve leaflets, while if extending substantially out of the plane, the post simply functions to connect and modify the shape of opposite sides of the annulus. The post may be length adjustable to allow variable modification of the annulus and may include additional posts of adjustable length or fixed length. As with other embodiments of the invention, the support structure may comprise a ring-shaped member or one or more discrete support segments.

As another manner of correcting an ischemic condition, for example, a ring-shaped support member is provided having an asymmetric-shape about two perpendicular axes. Stated more generally, one side of the ring-shaped support member may be of narrower width than an opposite side of the ring-shaped support member. This may or may not be coupled with a slight angling downward of one side of the ring-shaped support member with respect to the opposite side of the ring-shaped support member. These modifications help to close a gap created between the valve leaflets due to conditions such as an ischemic condition.

In another aspect of the invention, a device is provided for adjusting the distance between a papillary muscle and an annulus of a heart valve. This device comprises a support member configured to be affixed to the annulus of the heart valve and an elongate flexible tensile member having first and second ends with the first end adapted to be fixed to the papillary muscle. A connector is configured to connect with the elongate flexible member and with the support member in a manner allowing adjustment in the length between the papillary muscle and the support member and fixation of the elongate flexible member at a desired length between the papillary muscle and the support member. Generally, this device is useful for setting the critical distance between the papillary muscle and the valve annulus and may be used in preparation for the various valve replacement and repair techniques and devices disclosed herein.

In another aspect of the invention, a device is provided for supporting a heart valve in a patient and generally comprising a support member adapted to be affixed to the annulus and having at least one selectively adjustable portion allowing one section of the support member to be moved with respect to another section thereof and locked in place in order to maintain one or both of the annulus and the leaflets in a desired configuration. The support member may be ring-shaped, for example, and may be selectively adjustable such that one section, lying in a single plane, may be adjusted and angled away from a plane containing another section of the ring-shaped support member. Alternatively, or in addition, the ring-shaped support member may be adjustable to allow one section to be narrowed in width with respect to another section. This feature is also advantageous for correcting ischemic conditions.

In one general method of supporting a heart valve in accordance with the invention, a support structure is first connected to the heart valve annulus. A post is then fixed to the support structure, or the support structure may already have a post extending therefrom. The post is then connected to one of the valve leaflets to support the leaflets during opening and closing thereof. In accordance with the various aspects of this invention, the post may be connected to the leaflet with a flexible tensile member, such as a natural or artificial chord, or may be more directly connected to the leaflet. One direct connection includes extending a wire coil from the post into two adjacent leaflets to connect central portions of leaflets together. Other possible connections include the artificial or natural chord connections mentioned above.

Various objectives, features and advantages of the invention will become more readily apparent to those of ordinary skill in the art upon review of the following detailed description taken in conjunction with the the accompanying drawings.

BRIEF DESCRIPTION OF THE DRAWINGS

FIG. 7 is a perspective view of a second embodiment of the invention shown affixed to a mitral valve.

FIG. 7A is an alternative embodiment similar to the embodiment shown in FIG. 7.

FIG. 15 is another alternative embodiment of a support device shown affixed to a heart valve.

DETAILED DESCRIPTION OF THE PREFERRED EMBODIMENTS

Figure 1:
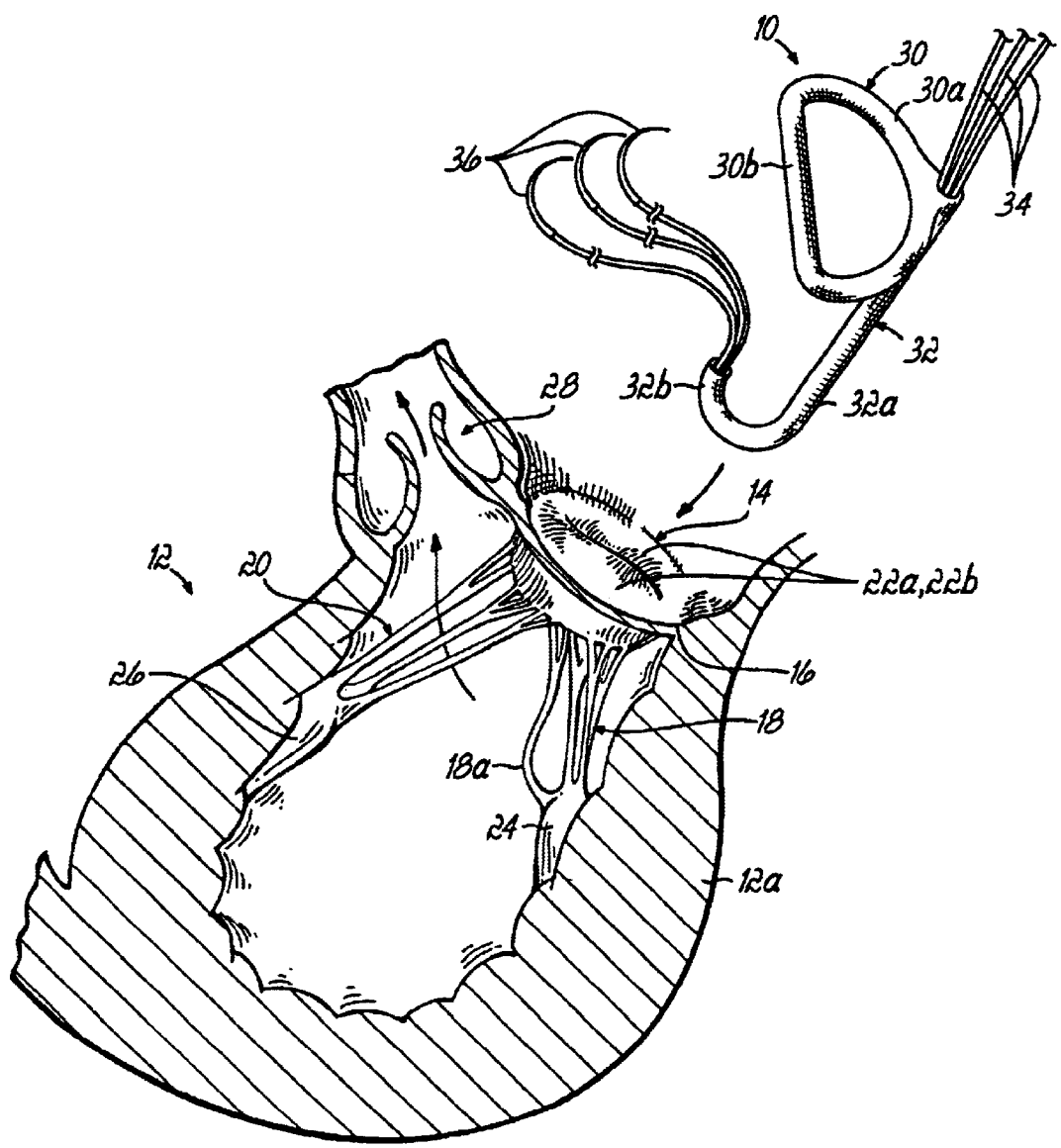
FIG. 1 is a perspective view of a first embodiment of the present invention being applied to a heart shown in partial cross section.

Referring first to FIG. 1, a device 10 for supporting a heart valve in a patient is shown. In the illustrated example, the left ventricle 12 of a patient's heart is shown in cross section with a mitral valve 14 for supplying blood into the ventricle 12. Mitral valve 14 includes an annulus 16 generally lying in a plane and a plurality of native chordae tendonae or chords 18, 20 respectively connected with a pair of valve leaflets 22a, 22b at one end and papillary muscles 24, 26 at an opposite end. In a normally functioning heart, chords 18, 20 support the valve leaflets 22a, 22b between open and closed positions to selectively allow and prevent blood flow into and out of left ventricle 12. Blood enters left ventricle 12 through mitral valve 14 and is expelled during the subsequent contraction of the heart muscle through aortic valve 28. It will be appreciated that the present invention is applicable to heart valves other than the mitral valve in various of its aspects to be described below.

Device 10 more particularly includes a support member 30 configured for attachment to the heart valve annulus 16 and a post 32 extending from support member 30 and configured to extend away from the plane of annulus 16. A connector which, in this embodiment, is in the form of at least one flexible tensile member, is coupled with post 32 and configured for attachment to at least one of the leaflets 22a, 22b. In this embodiment of the invention, post 32 is a hollow, J-shaped member having a longer section 32a and a shorter curved section 32b. Also, post 32 may be hollow as shown with flexible tensile members 34 extending through the post and exiting at shorter section 32b. Flexible tensile members 34 may include suture needles for affixing the tensile members to the edges of the valve leaflets 22a, 22b as described below. Other connectors suitable for directly or indirectly coupling post 32 or a post of different configuration to valve leaflets 22a, 22b may be utilized as well and some variations are described herein below.

Figure 2:
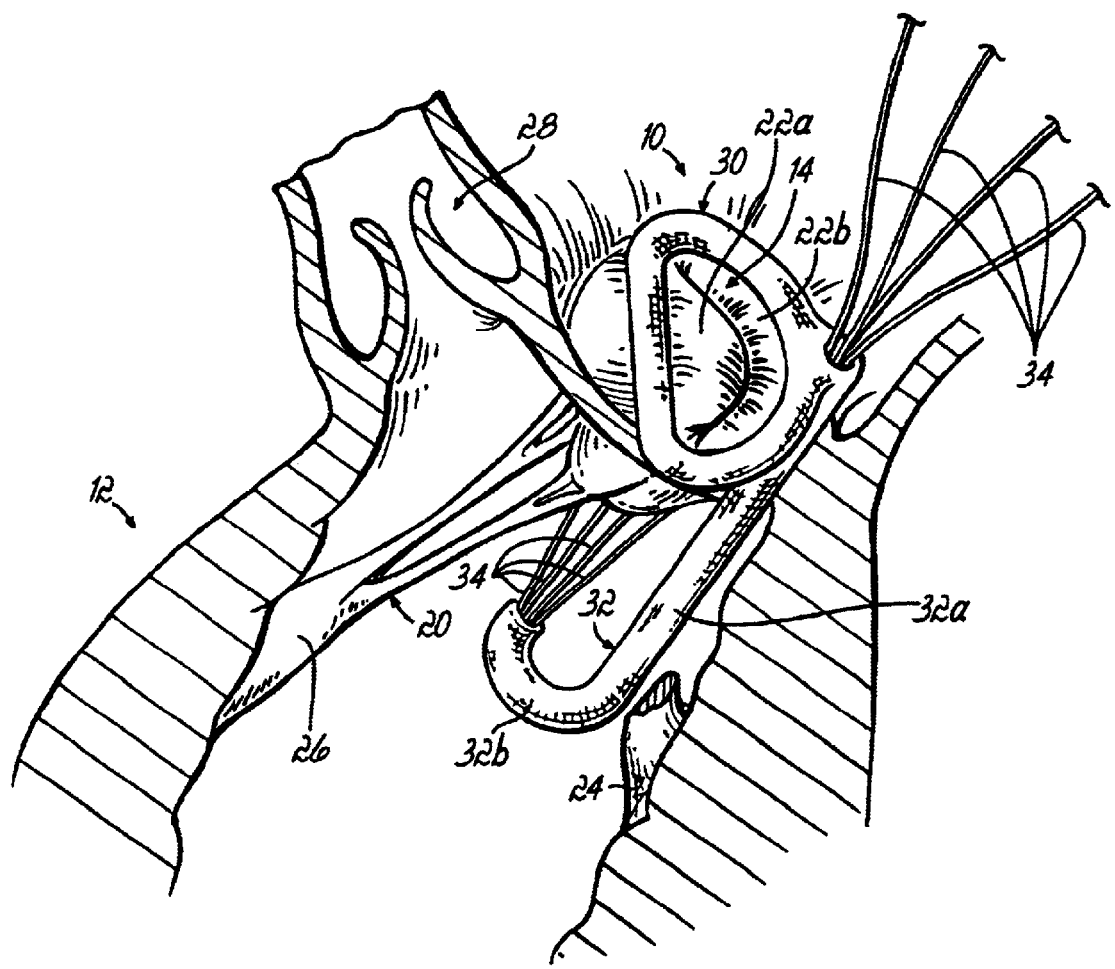
FIG. 2 is a perspective, partially sectioned view similar to FIG. 1 but enlarged and showing the device of this invention affixed to the mitral valve.
Figure 3:
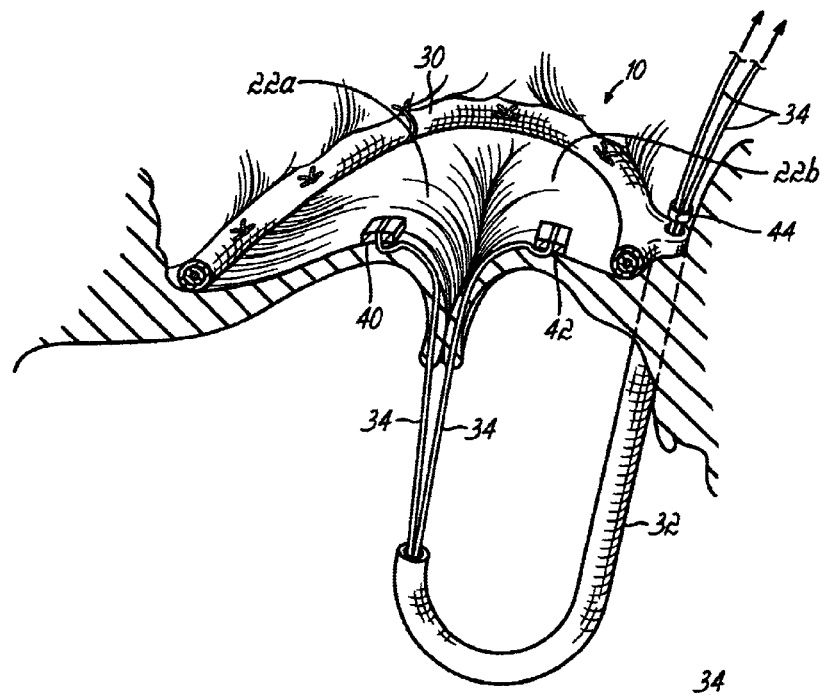
FIG. 3 is a perspective, partially sectioned view of the device shown in FIGS. 1 and 2 with the mitral valve shown in cross section.
Figure 5:
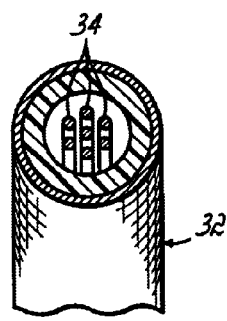
FIG. 5 is a cross sectional view taken along line 5—5 of FIG. 4.
Figure 4:
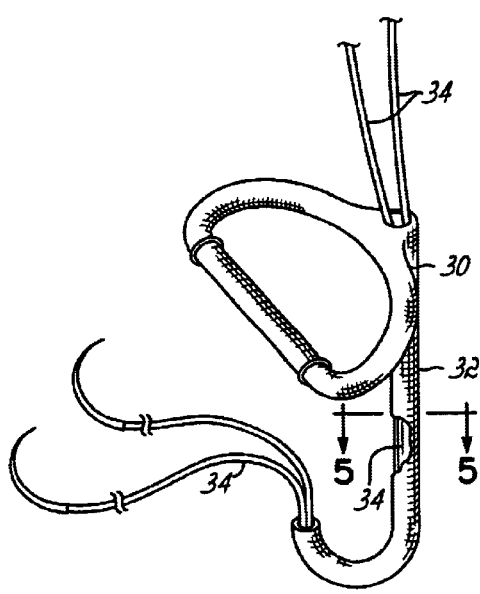
FIG. 4 is a partially fragmented, perspective view of the device shown in FIGS. 1–3.
Figure 6:
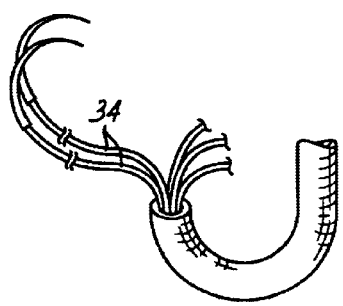
FIG. 6 is a fragmented perspective view of a device similar to that shown in FIG. 4, but illustrating additional flexible tensile members or artificial chords.

As shown in FIG. 2, flexible tensile members 34 may completely substitute for one set of chordae tendonae 18 (FIG. 1) or, as an alternative, one or more defective chords, such as a lengthened chord 18a (FIG. 1), may be replaced with an artificial chord or flexible tensile member in accordance with the invention. As shown in FIG. 2, all of the native chords 18 of the patient have been removed and device 10 has been affixed by suturing ring-shaped support 30 to valve annulus 16 using stitches (not shown) and by affixing flexible tensile members or artificial chords 34 to leaflets 22a, 22b. Flexible tensile members 34 may be affixed to mating edges of valve leaflets 22a, 22b by being stitched thereto as shown in FIG. 3 using suitable pads or suture supports 40, 42. It will be appreciated that the remaining native chords and other artificial chords have been omitted in FIG. 3 for clarity. A crimp member 44 is also shown in FIG. 3 for fixing flexible tensile members 34 at the desired length. That is, after chords 34 have been affixed to valve leaflets 22a, 22b as shown in FIG. 3, the distance between the lower edges of leaflets 22a, 22b and section 32b of post 32 may be adjusted to ensure effective coaptation or mating of the valve leaflets 22a, 22b. When this is achieved, crimp member 44 is crimped onto flexible tensile members 34 to retain flexible tensile members 34 at this distance and maintain the effective coaptation. Ring-shaped support member 30 may be comprised of two integrated sections with one being a curved section 30a and one being a straight section 30b as is the case with certain conventional annuloplasty rings. FIGS. 4, 5 and 6 illustrate the hollow nature of the support post and the use of a number of flexible tensile members or artificial chords 34, depending on the patient's needs.

FIGS. 7 illustrates a device 50 constructed in accordance with one alternative embodiment. in this embodiment, a valve annulus support member 52 is again shown as a ring-shaped member and a post 54 extends away from ring-shaped support member 52. Post 54 includes at least one chord gripping member 56 comprised of a pair of jaws 56a, 56b. In this embodiment, a second chord gripping member 58 is shown also comprising a pair of jaws 58a, 58b. Gripping member 56 is shown as gripping anterior native chords of the patient, while gripping member 58 is shown to grip posterior native chords of the patient. The purpose of device 10 is to retain the use of the patient's native chords 18, but to more fully restore their function. In cases in which a patient's heart is ischemic, there may be stretched or lengthened chords, such as chord 18a shown in FIG. 1. In this case, device 50 and, more particularly, gripping members 56, 58 may be used to capture chords 18 and place them under suitable tension mimicking their natural, normal condition to provide full support to valve leaflets 22a, 22b. FIG. 7A illustrates an alternative embodiment similar to FIG. 7, but having a annulus support portion 52' which is not ring-shaped, but neverthel ss provides suitable support when attached to a valve annulus for supporting post 54. It will be appreciated that, while this embodiment is especially suitable for use on a patient's native chords, similar chord gripping members may be used to capture artificial chords, such as sutures or GOR-TEX (expanded polytetrafluoroethylene) fibers, connected with the valve leaflet edges as previously described. Jaws 56a, 56b and 58a, 58b may be formed in any suitable manner and may operate between open and closed positions also in any suitable manner.

Figure 8:
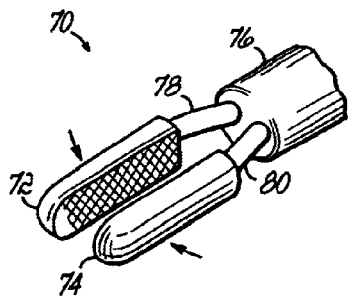
FIGS. 8–14 illustrate various alternative mechanisms for grasping a patient's native or artificial chords and useable in conjunction with the embodiment of FIGS. 7 and 7A.

FIGS. 8–14 illustrate several different illustrative examples of mechanisms for opening and closing the jaws of a gripping member suitable for use in the embodiments of FIGS. 7 and 7A. FIG. 8 illustrates a gripping member 70 comprised of jaws 72, 74 connected with a post 76 by respective shape memory rods 78, 80. When electric current or heat is applied to rods 78, 80, jaws 72, 74 move together into a clamped or closed position.

Figure 9:
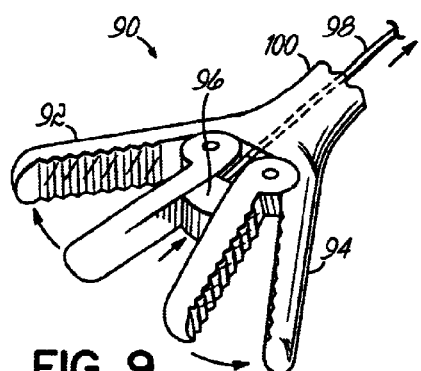

In FIG. 9, gripping structure 90 is shown as comprising a pair of hinged jaws 92, 94 operable by a cam member 96 and an actuating wire 98 contained within a post 100. When wire 98 is pulled and fixed, cam member 96 will cam jaws 92, 94 into closed or clamped positions on the patient's native or artificial chords.

Figure 10:
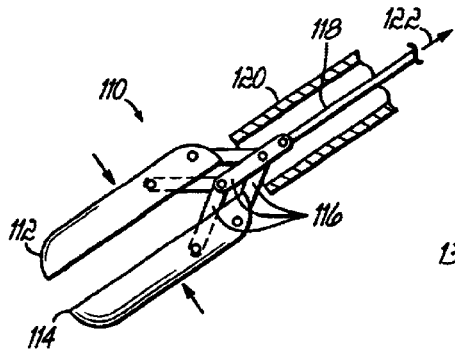

FIG. 10 illustrates a chord gripping member 110 comprised of first and second jaws 112, 114 pivotally connected together by a series of links 116 and operable between open and closed positions by a wire 118 contained within a post 120. When wire 118 is pulled in the direction of arrow 122, and fixed, links 116 will move jaws 112, 114 to the closed position.

Figure 11:
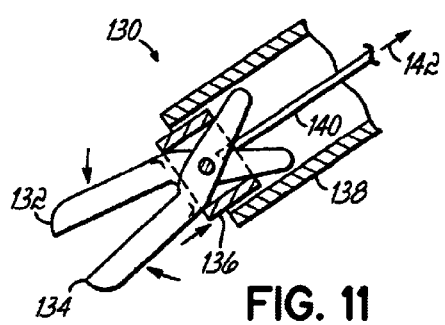

FIG. 11 illustrates a chord gripping member 130 comprising a pair of jaws 132, 134 hingedly connected together and contained within an actuating member 136 fixed within a post 138. When wire 140 is pulled in the direction of arrow 142, jaws 132, 134 will be forced by actuating member 136 into their closed and clamped position. Wire 140 may then be fixed in this position by any suitable means.

Figure 12:
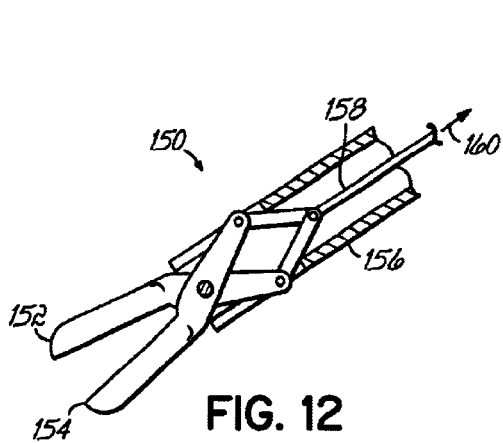

FIG. 12 illustrates another alternative gripping member 150 comprised of first and second jaws 152, 154 hingedly connected together and pivotally secured to a hollow post 156. A wire 158 is connected to the ends of jaws 152, 154 and when pulled in the direction of arrow 160 jaws 152, 154 will be actuated to their closed and clamped positions. Again, wire 158 may be fixed in any suitable manner once gripping member 150 is in the closed and clamped position.

Figure 13:
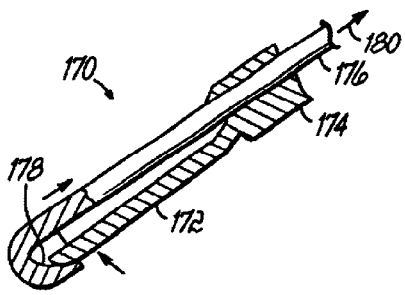

FIG. 13 illustrates a gripping member 170 comprised of a movable jaw 172 hingedly or flexibly connected with a post 174 and operable by a wire or movable actuating member 176. An outer end of jaw 172 is retained against a cam surface 178 of actuating member 176. When actuating member 176 is pulled in the direction of arrow 180, jaw 172 will be forced to close against member 176 and clamp the native or artificial chords therebetween. Actuating member 176 may be fixed in any suitable manner at this position.

Figure 14:
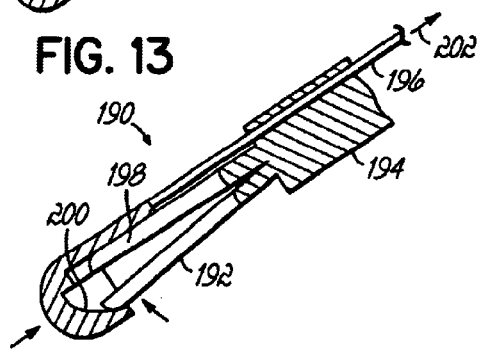

FIG. 14 illustrates another alternative clamping member 190 comprised of a movable jaw 192 hingedly or flexibly connected with a post 194 and operable between open and closed positions by an actuating member or wire 196 which slides with respect to a stationary jaw 198. Movable jaw 192 has one end retained against a cam surface 200. When actuating member or wire 196 is pulled in the direction of arrow 202, jaw 192 will be forced to a closed and clamped position against jaw 198 by way of the camming action of surface 200. Wire or actuating member 196 may be fixed at this position by any suitable means.

FIG. 15 illustrates another alternative valve support 210 constructed in accordance with the invention. In this embodiment, valve support 210 may be used as a support for a replacement heart valve 212, which may be formed from artificial or biological material. Valve support device 210 more specifically comprises a pair of ring-shaped support members 214, 216 with ring support member 214 being connected with the annulus of valve 212. Ring-shaped support member 216 is connected to support member 214 in spaced relation by a series of posts 218, 220, 222, 224. This structure supports a series of flexible tensile members, or artificial chords 226, 228, 230, 232 connected to the edges of valve leaflets 234, 236 in a suitable manner, such as in the manner described with respect to the first embodiment.

Figure 16:
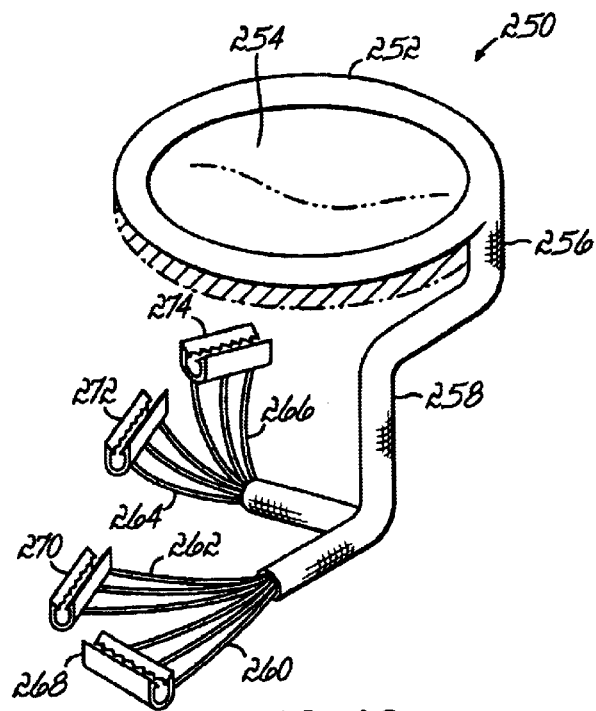
FIG. 16 is another alternative embodiment of a support device for a heart valve.

FIG. 16 illustrates another alternative valve support device 250 including a ring-shaped support member 252 configured to be connected with the annulus of a heart valve 254 and including a post 256 connected therewith. In this embodiment, post 256 includes a section 258 extending inwardly toward the center of heart valve 254. This spaces post 256 away from any potentially harmful contact with the inner wall of the heart muscle. A series of flexible tensile members or artificial chords 260, 262, 264, 266 extend outwardly from post 258 and include respective grippers 268, 270, 272, 274. Grippers 268, 270, 272, 274 may be used as alternatives to directly stitching these artificial chords to the valve leaflets. Instead, these grippers may simply be clamped onto the edges of the valve leaflets to provide the same function as the attachment shown and described with respect to FIG. 3, for example.

Figure 17:
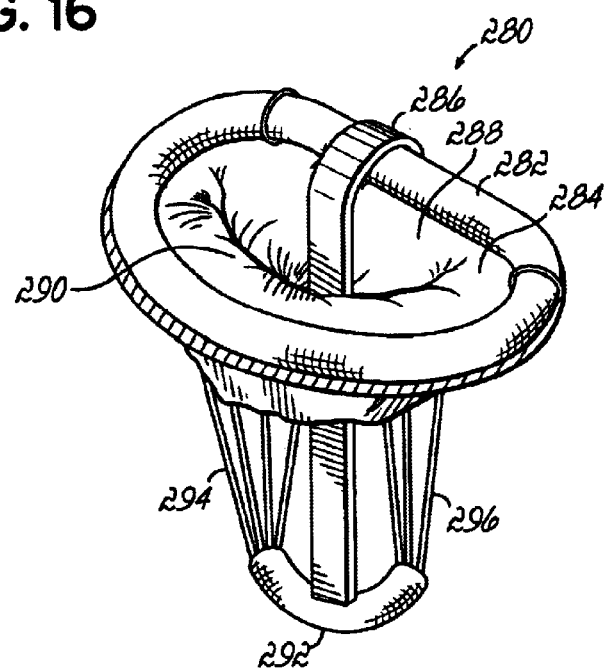
FIG. 17 is a perspective view of another alternative embodiment of a support device shown affixed to a heart valve.

FIG. 17 illustrates another alternative valve support device 280 comprised of a ring-shaped support member 282 fixed to a heart valve 284 in any suitable manner and including a post 286. Post 286 is preferably rigidly secured to ring-shaped support member 282 and extends through the center thereof so as to be configured to extend between the valve leaflets 288, 290. Post 286 is connected with or integrally includes a chord supporting portion 292 at an opposite end and, as with the other embodiments, flexible tensile members or artificial chords 294, 296 are connected between support portion 292 and valve leaflets 288, 290.

Figure 18:
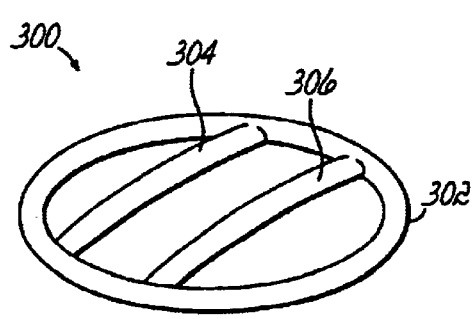
FIG. 18 is a perspective view of another alternative support device for a heart valve.

FIG. 18 illustrates an alternative valve support device 300 comprised of a ring-shaped support member 302 and preferably a pair of posts 304, 306. Ring-shaped support member 302 is configured to be affixed to the annulus of a heart valve, as with various other embodiments of this invention, while posts 304, 306 are configured to prevent outward billowing of the heart valve leaflets. For this purpose, posts 304, 306 may be slightly curved, as shown, in an outward direction with respect to the heart valve beneath.

Figure 19:
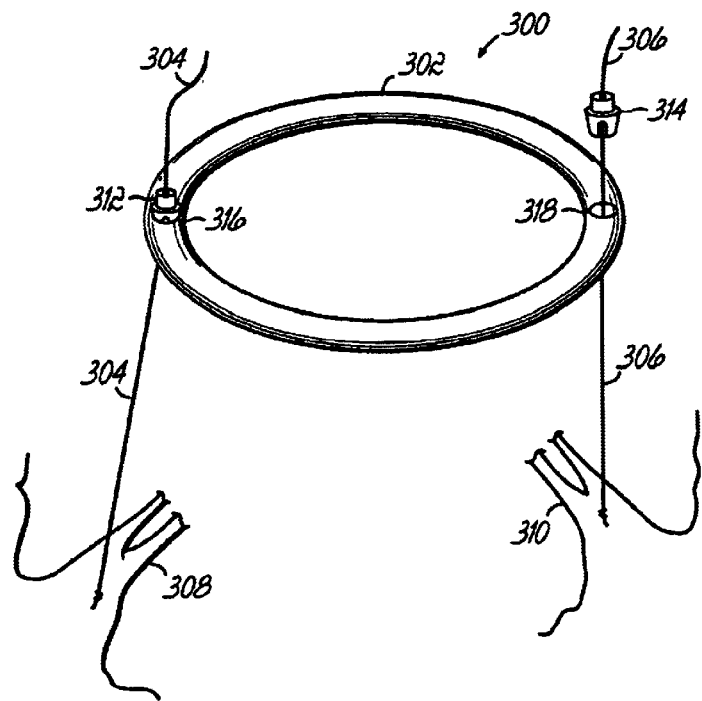
FIGS. 19 and 20 are perspective views of alternative devices used to establish a distance between a heart valve support ring and the papillary muscles of a patient.

FIG. 19 illustrates a device for setting the distance between the annulus of the mitral heart valve and the patient's papillary muscles. In particular, device 300 comprises a ring-shaped support member 302 configured to be sutured or otherwise affixed to the annulus of the heart valve and a pair of flexible tensile members 304, 306, which may be sutures, connected between the respective papillary muscles 308, 310 of the patient and the ring-shaped support member 302. In this embodiment, to facilitate connection with ring-shaped support member 302, tensile members 304, 306 are slidably retained on crimp members 312, 314 while the length or distance between papillary muscles 308, 310 and ring-shaped support member 302 is set. Crimp members 312, 314 may then be forced into respective holes 316, 318 and thereby crimped to tensile members 304, 306 to simultaneously affix crimp members 312, 314 to ring-shaped support member 302 and to the corresponding tensile member 304, 306.

Figure 20:
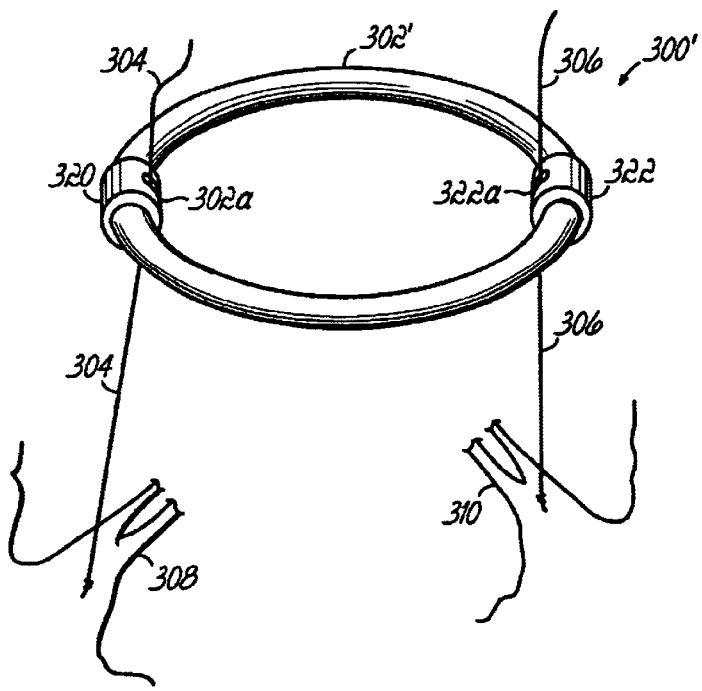

FIG. 20 illustrates an alternative device 300' for setting the distance between a ring-shaped support member 302' and the respective papillary muscles 308, 310. In FIG. 20, reference numerals with prime (') marks indicate subject matter similar to the corresponding reference numerals in FIG. 19, while like numerals indicate like elements between these figures. Device 300' includes a ring-shaped support member 302' configured to be connected to a heart valve annulus and including two connectors 320, 322 that affix tensile members 304, 306 to ring-shaped support members 302' after ring-shaped support member 302' has been affixed to a heart valve annulus, a surgeon stitches flexible tensile members 304, 306 to papillary muscles 308, 310 and after adjusting the distance properly between papillary muscles 308, 310 and ring-shaped support member 302', affixes tensile members 304, 306 to connectors 320, 322. These connectors 320, 322 may include slots 320a, 322a which allow flexible tensile members 304, 306 to become wedged and retained therein.

Figure 21:
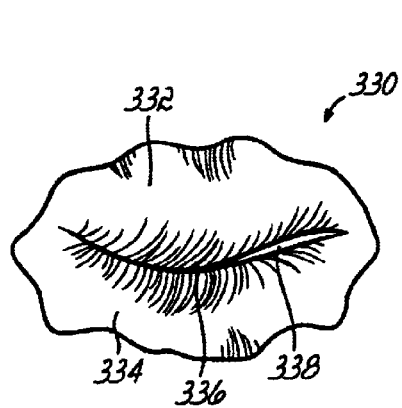
FIG. 21 is a fragmented view showing a heart valve with a malformation caused by an ischemic heart muscle.

FIG. 21 illustrates a heart valve 330 comprised of first and second leaflets 322, 334 that engage one another at an area of coaptation 336 defining a selectively opened and closed portion of the valve. Valve 330 has a malformation, however, in the form of a gap 338 that is typically the result of an ischemic condition which pulls one portion or leaflet of the valve away from the other.

Figure 22:
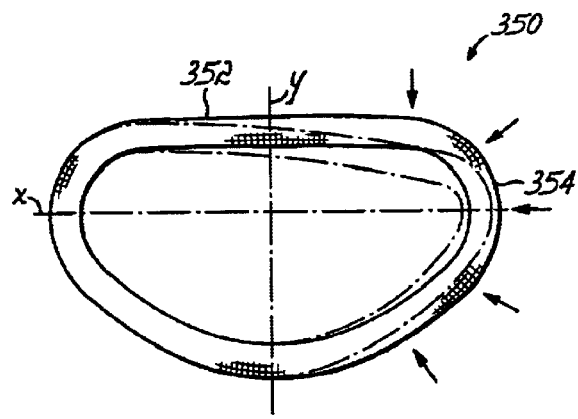
FIG. 22 is an elevational view of a support ring having an adjustability feature in accordance with the invention.
Figure 22A:
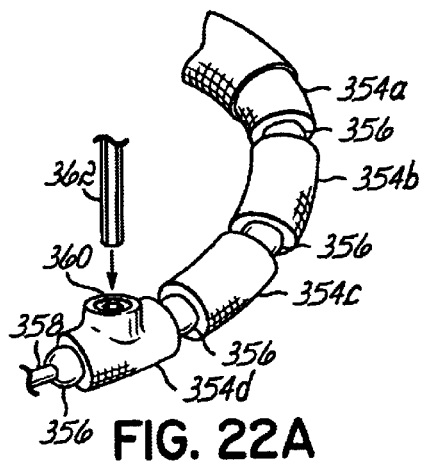
FIG. 22A is a perspective view showing a portion of the ring of FIG. 22 and an adjustability feature thereof.
Figure 23:
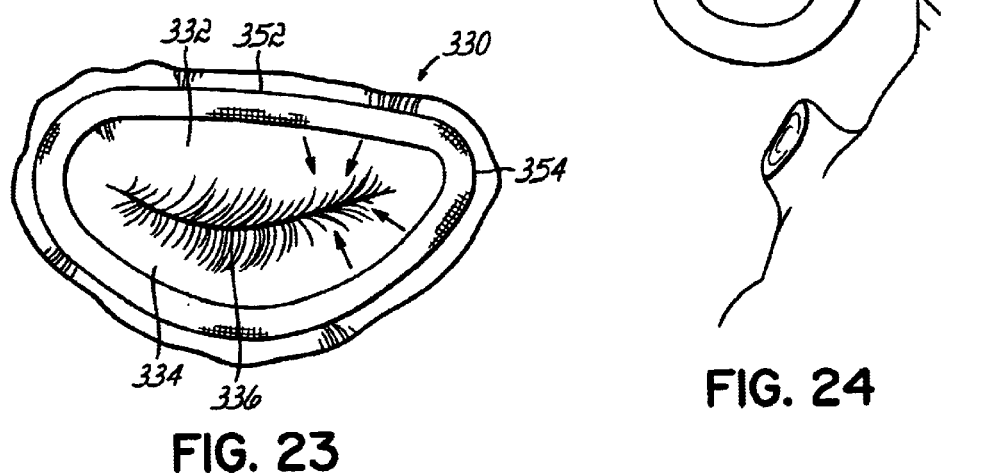
FIG. 23 is an elevational view showing the ring of FIG. 22 applied to correct the malformation shown in FIG. 21.

FIGS. 22, 22A and 23 illustrate a valve support device 350 for correcting valve malformations such as that shown in FIG. 21. These devices are especially useful for treating ischemic conditions in which one side of the valve pulls away from another side resulting in imperfect coaptation of the valve leaflets. Specifically, device 350 is in the form of a ring-shaped support member 352 having a selectively adjustable and lockable portion 354. As shown best in FIG. 22, ring-shaped support member 352 may be reformed into the shape shown in phantom and retained in that shape. Alternatively, device 350 may be formed with a permanent asymmetric shape about both axes x,y. As shown in FIG. 23, the ability to squeeze portion 354 of ring-shaped support member 352 together and retain portion 354 in that position will bring valve leaflets 332, 334 together to close gap 338. FIG. 22A illustrates one manner of allowing selectively adjustable and lockable positioning of ring-shaped support member 352. In this regard, respective socket segments 354a, 354b, 354c receive balls 356 therebetween and further receive a wire 358 which may be tensioned and locked in place with a set screw 360 by use of a tool 362. When wire 358 and socketed segments 354a–d and balls 356 are loosened, adjustability of section 354 is possible. Once the adjustment in position is made, wire 358 is tensioned to bring the balls and sockets together and then lock in place using tool 362. This retains the adjusted shape.

Figure 24:
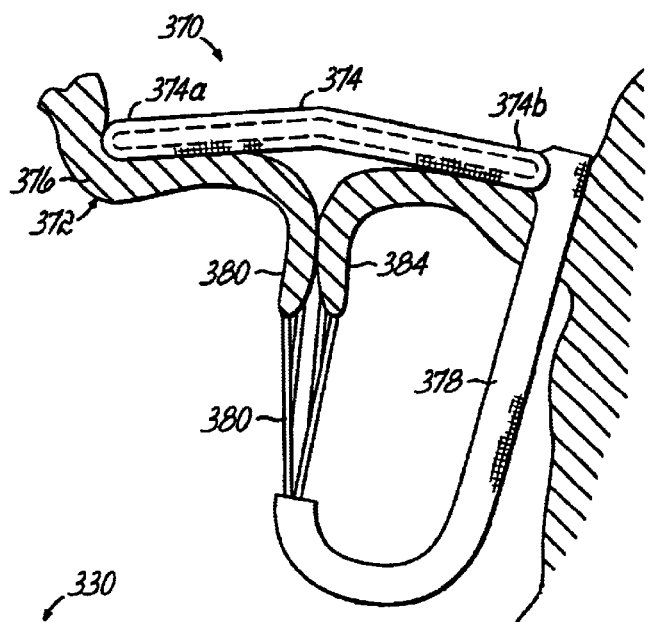
FIG. 24 is a partially sectioned view showing an adjustable ring or heart valve support member connected to a heart valve and used in conjunction with a post of the present invention.

FIG. 24 illustrates another alternative device 370 for supporting a heart valve 372. Device 370 again comprises a valve support member 374 adapted to be connected with the valve annulus 376, such as by suturing or other mechanical fastening means. A post 378 and flexible tensile members 380 are connected with support member 374 as described generally above to support valve leaflets 382, 384. In this embodiment, one portion 374a of valve support member 374 may be bent out of the plane containing another portion 374b and retained in that position to fix the valve in a desired position. Any suitable manner of retaining the adjusted shape may be used, including the manner described with respect to FIG. 22A. Alternatively, device 370 may be permanently formed with a nonplanar shape, such as the shape shown in FIG. 24. The modified shape shown in phantom in FIG. 22 may also, be combined with the modified shape shown in FIG. 24 for ring-shaped support member 374.

Figure 25:
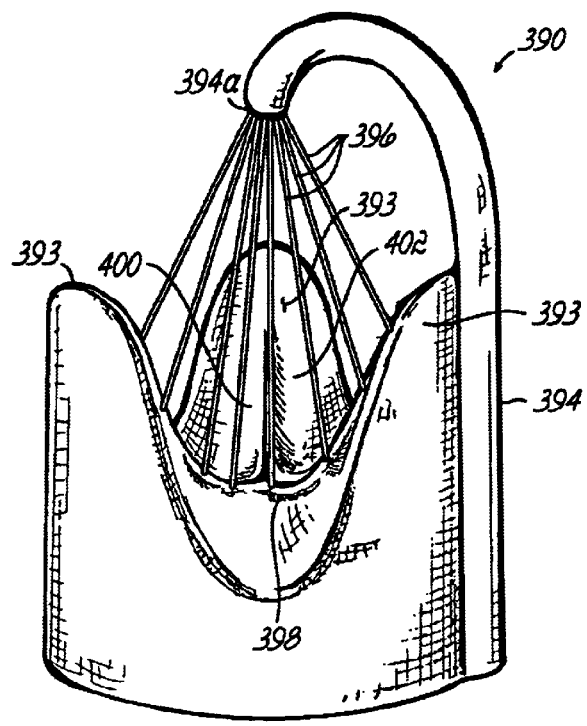
FIG. 25 is a perspective view of an alternative heart valve and heart valve support.

FIG. 25 illustrates another alternative valve support device 390 incorporating a replacement heart valve 392 with the support structure including a post 394 and a plurality of flexible tensile members or sutures 396 extending from an end 394a of post 394 and edges of three leaflets 398, 400, 402 associated with valve 392. Flexible tensile members 396 are preferably distributed evenly along the edges of leaflets 398, 400, 402 to support the leaflets during operation with proper coaptation or mating of the adjacent leaflet surfaces. Flexible tensile members 396 also reduce stress on commisures 393.

Figure 26:
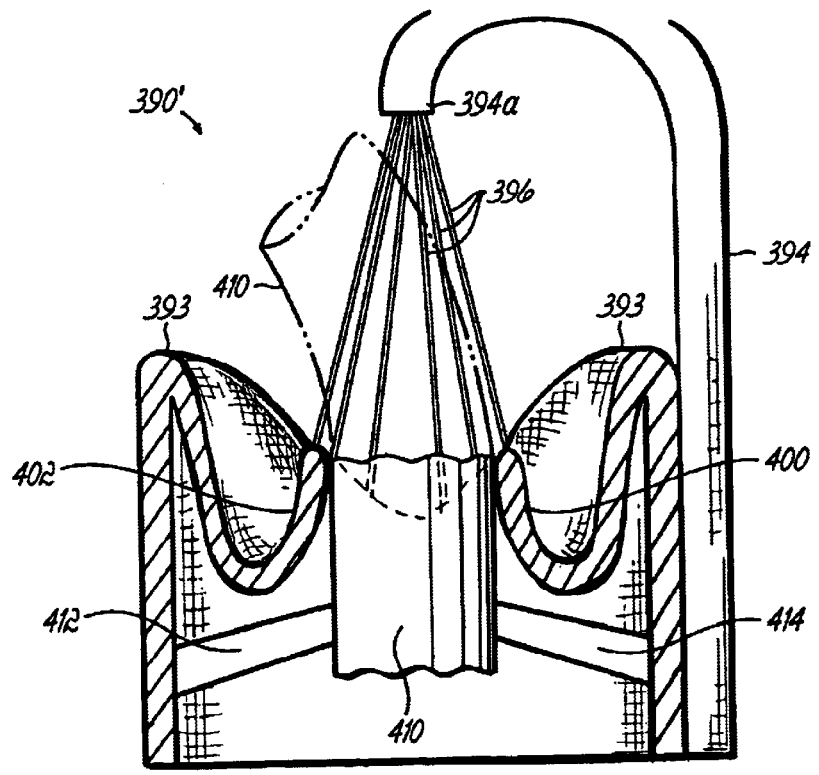
FIG. 26 is a partially sectioned view of the device shown in FIG. 25 with a catheter inserted through the heart valve.

FIG. 26 illustrates a cross sectional view of a somewhat modified form 390' of support device 390 having a catheter inserted between the valve leaflets 398, 400, 402. In this embodiment, flexible tensile members 396 prevent leaflets 398, 400, 402 from opening and closing against catheter 410 with excessive force. This is in addition to stress reduction on commisures 393. Such force may be harmful to valve 392. Catheter 410 may be support within valve 392 by suitable struts or other support members 412, 414.

Figure 27:
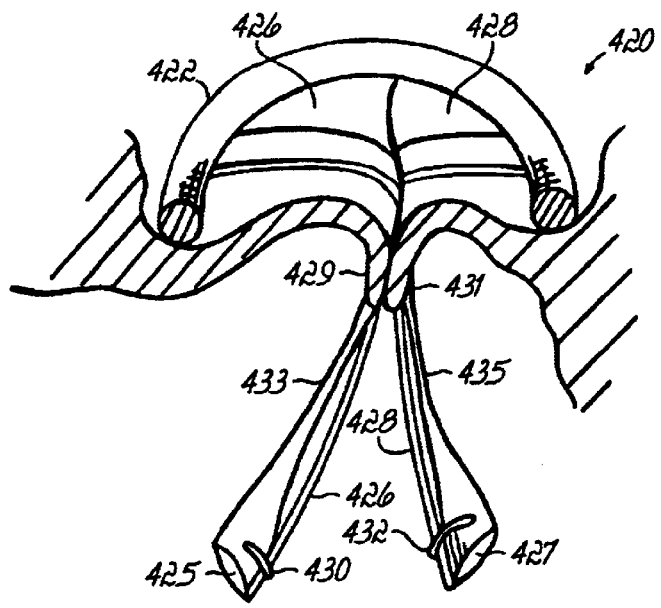
FIG. 27 is a perspective, partially sectioned view of a device for establishing the distance between the heart valve and the papillary muscles of a patient.

FIG. 27 illustrates another alternative device in the form of a ring-shaped valve support member 422 configured to be affixed to the annulus 424 of a heart valve. Device 420 is used to set the distance between the ring-shaped support member 422 and the papillary muscles 425, 427 of the patient. A pair of posts 426, 428 extend generally in a radially inward direction from ring-shaped support member 422 and are directed through the center of the valve between leaflets 429, 431 and down along the patient's native chords 433, 435. Posts 426, 428 are affixed to the patient's papillary muscles 425, 427 at the desired location. This suitable fixes the location of chords 433, 435 and allows the surgeon to use any of the other valve support devices contemplated by this invention to facilitate supporting the leaflets 429, 431 for proper coaptation. Once the appropriate valve support device or devices are in place to properly support leaflets 429, 431, device 420, or at least posts 426, 428, may be removed.

Figure 28:
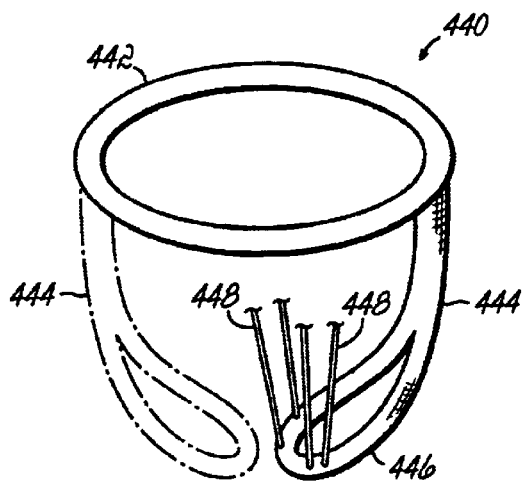
FIG. 28 is a perspective view of an alternative heart valve support device of the present invention.

FIG. 28 illustrates another alternative valve support device 440 comprised of a ring-shaped support member 442 configured for attachment to the annulus of a heart valve and a post 444 connected to support member 442 and including an annular or loop-shaped end 446. As with previous embodiments of the invention, one or more flexible tensile members or artificial chords may be affixed to end portion 446 and connected at an opposite end to one or more valve leaflets (not shown). Post 444, and especially loop-shaped end portion 446, provides a resilient structure for bearing against the internal wall of the heart muscle. At least end portion 446 can flex in a resilient fashion toward ring-shaped support member 442 as the heart muscle contracts and moves. This reduces the likelihood of injury to the heart muscle and provides an artificial chord support that more naturally mimics the operation of a papillary muscle.

Figure 29:
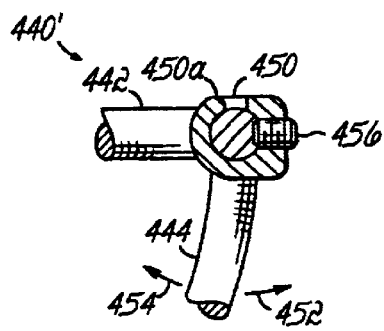
FIG. 29 is a fragmented, partially sectioned view showing an adjustability feature between the post and the heart valve support member of this invention.

FIG. 29 illustrates an alternative valve support device 440', which may be configured similarly to valve support device 440, except that post 444 is connected to ring-shaped support member 442 by an adjustable and lockable connection 450. This allows adjustment in the direction or arrows 452, 454. After the appropriate adjustment is made, post 444 may be locked in the desired position with a set screw 456 tightened against ring-shaped support member 442. A slot 450a also allows post 444 to be completely removed from support member 442.

Figure 30:
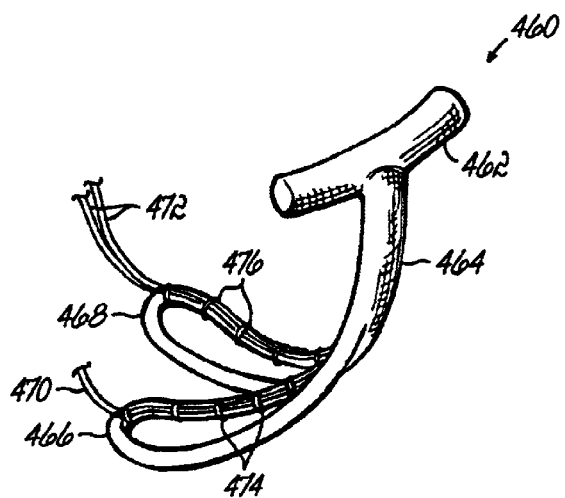
FIG. 30 is a perspective view of an alternative heart valve support device shown affixed to a heart valve.

FIG. 30 illustrates a valve support device 460 similar to device 440, but having a support member 462 which is not ring-shaped and having a post 464 with first and second loop-shaped end portions 466, 468. One or more flexible tensile members 470, 472 may be retained on post 464 and loop-shaped end portions 466, 468 by suitable rings 474, 476 allowing length adjustment of flexible tensile members 470, 472. Flexible tensile members 470, 472 may extend upwardly past support member 462 and may be tied thereto after length adjustment is made.

Figure 31:
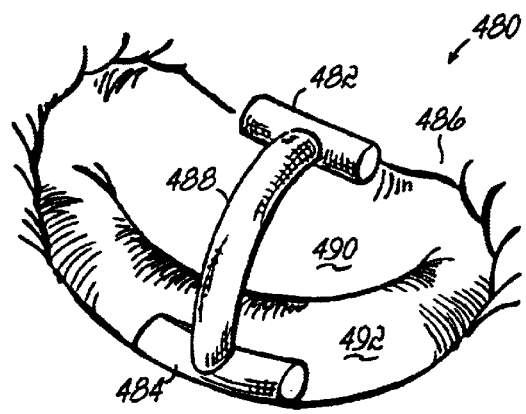
FIG. 31 is another alternative heart valve support device shown affixed to a heart valve.

FIG. 31 illustrates a valve support device 480 comprising separate support members 482, 484 affixed to opposite sides of a heart valve annulus 486. A post 488 connects support members 482, 484 together thereby affixing the position of these opposite portions of heart valve annulus 486 with respect to one another. This may be used to pull two valve leaflets 490, 492 together. Also, device 480 may be used to remodel the shape of annulus 486.

Figure 32:
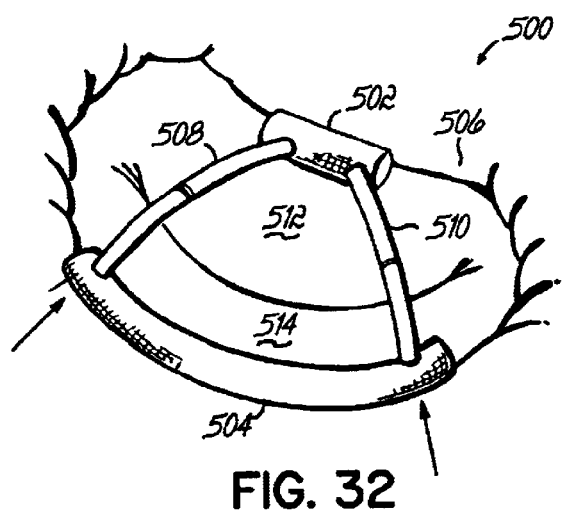
FIG. 32 is a perspective view of another alternative heart valve support device.

FIG. 32 is a valve support device 500 constructed in a similar manner to support device 480, but allowing further adjustability. Specifically, first and second valve annulus support members 502, 504 are respectively connected to opposite sides of a heart valve annulus 506. At least one and preferably two telescopically adjustable posts 508, 510 connect support members 502, 504 together. In the configuration shown, one or both posts 508, 510 may be adjusted in length depending on the particular malformation or abnormality of leaflets 512, 514. Once adjusted to the appropriate length by the surgeon, telescopic posts 508, 510 may be fixed at the desired length by any suitable means.

Figure 33:
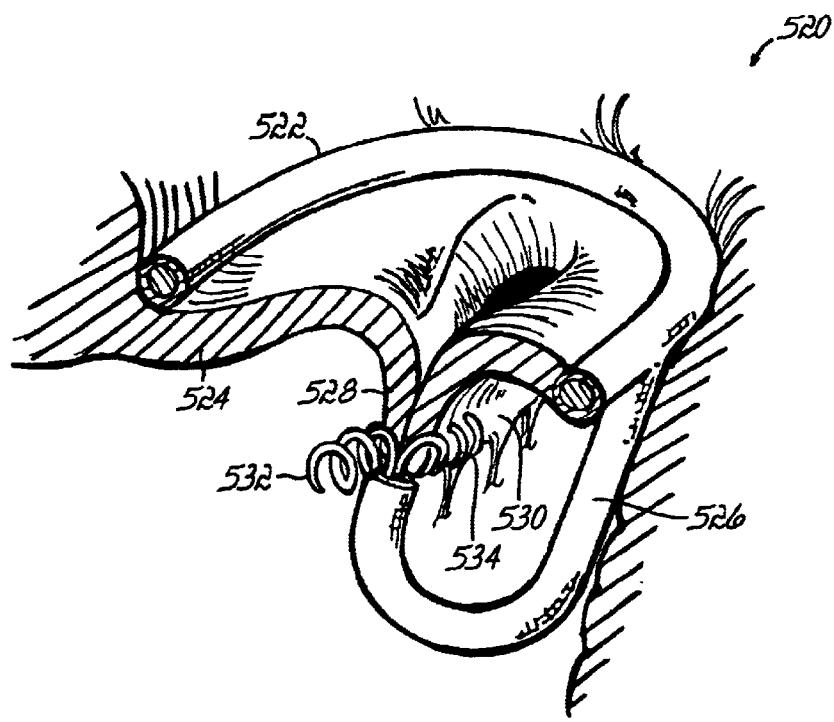
FIG. 33 is a perspective, partially sectioned view of another heart valve support device.

FIG. 33 illustrates another alternative valve support device 520 comprised of a ring-shaped support member 522 configured to be connected with a heart valve annulus 524 and a post 526 generally constructed with a J-shape as in certain previous embodiments. In this embodiment, however, post 526 connects directly with valve leaflets 528, 530 by way one or more spiral coil connectors 532, 534 extending outwardly from post 526. As the surgeon pushes these wires 532, 534 from post 526, they will form the coiled shape shown in the figure and simultaneously be directed through leaflets 528, 530 to connect these leaflets at a central location.

Figure 33A:
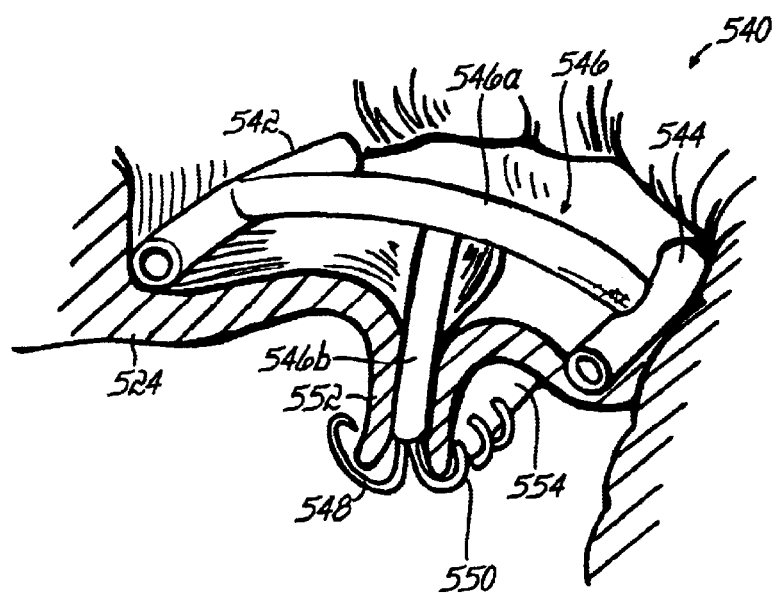
FIG. 33A is a perspective, partially sectioned view of another alternative heart valve support device.

FIG. 33A illustrates another valve support device 540 similar to device 520 but utilizing separate valve support members 542, 544 in place of a ring-shaped support member and further including a centralized post structure 546 comprised of post members 546a and 546b. Again, the surgeon will install this device by affixing support members 542, 544 to the heart valve annulus 524 and then as coiled wire connectors 548, 550 are pushed through post portion 546b, they will simultaneously be coiled and directed through valve leaflets 552, 554 to connect central portions thereof together.

While the present invention has been illustrated by a description of preferred embodiments and while these embodiments have been described in some detail, it is not the intention of the Applicants to restrict or in any way limit the scope of the appended claims to such detail. Additional advantages and modifications will readily appear to those skilled in the art. The various features and concepts of the invention may be used alone or in numerous combinations depending on the needs and preferences of the user. This has been a description of the present invention, along with the preferred methods of practicing the present invention as currently known. However, the invention itself should only be defined by the appended claims, wherein we claim:

What is claimed is:

1. A device for supporting a heart valve in a patient, the heart valve including an annulus generally lying in a plane and a plurality of leaflets connected therewith and having coapting edges adapted to open and close to selectively allow and prevent blood flow, the device comprising:

a support member configured for attachment to the heart valve annulus, and a post extending from said support member and configured to extend away from the plane of the annulus, and a connector coupled with said post and configured for attachment to at least one of said coapting edges of said leaflets.

2. The device of claim 1, wherein said connector is configured to connect one end of said post directly adjacent said one of said coapting edges.

3. The device of claim 1, wherein said support member is ring-shaped and includes a straight section connected with a curved section.

4. The device of claim 1, wherein said post is generally J-shaped with a long section and a shorter section, said long section connected to said support member and said shorter section coupled with said connector.

5. The device of claim 1, wherein said post has a blunt contact surface configured for insertion and retention within the heart chamber without damaging the heart during or after implantation.

6. The device of claim 1, wherein said post is configured to extend radially outside the annulus of said valve when affixed thereto.

7. A device for supporting a heart valve in a patient, the heart valve including an annulus generally contained an a plane and a plurality of leaflets having coapting edges adapted to open and close to selectively allow and prevent blood flow, said leaflets being supported by a plurality of artificial or natural chords, the device comprising:

a support member configured for attachment to the heart valve annulus, at least one post extending from said support member and configured to extend away from the plane of the annulus, and a first chord gripping member coupled with said post and configured to releasably clamp at least one of said chords at adjustable positions along the length of said one chord and thereby fixes a desired portion of the length of said one chord between said first chord gripping member and one of the coapting edges of said leaflets thereby supporting and aligning said leaflets for coaptation during operation of the valve.

8. The device of claim 7, wherein said first chord gripping member further comprises a pair of movable jaws adapted to grip the first plurality of chords therebetween.

9. The device of claim 7, further comprising a second chord gripping member configured to grip a second plurality of said chords and thereby fix the length of said second plurality of said chords between said second chord gripping member and said leaflets to support and align said leaflets for coaptation during operation of the valve.

10. The device of claim 9, wherein said first and second chord gripping members each further comprises a pair of movable jaws adapted to grip the first and second pluralities of chords respectively therebetween.

11. The device of claim 7, wherein at least a portion of said first chord gripping member is formed of shape memory material allowing remote actuation thereof to grip the first plurality of chords.

12. The device of claim 7, further comprising an actuating structure coupled with said first chord gripping member and configured to move a portion of said first chord gripping member with respect to another portion of said first chord gripping member to grip the first plurality of chords.

13. The device of claim 7, wherein said support member is ring-shaped.

14. The device of claim 7, wherein said support member is shaped as a ring segment.

15. The device of claim 7 further comprising a replacement heart valve attached to said support member.

* * * * *